US010328292B2

(12) United States Patent
Kanakala et al.

(10) Patent No.: US 10,328,292 B2
(45) Date of Patent: Jun. 25, 2019

(54) MULTI-SENSOR BASED MOTION SENSING IN SCBA

(71) Applicant: Honeywell International Inc., Morristown, NJ (US)

(72) Inventors: LG Srinivasa Rao Kanakala, Hyderabad (IN); Praveen Kumar Palacharla, Hyderabad (IN); Rahul Ramesh Bhaskarwar, Hyderabad (IN); Jeffrey Shipley, Rancho Santa Margarita, CA (US); Gregory Vrablik, Brea, CA (US); Mark Fischer, Mission Viejo, CA (US)

(73) Assignee: Honeywell International Inc., Morris Plains, NJ (US)

( * ) Notice: Subject to any disclaimer, the term of this patent is extended or adjusted under 35 U.S.C. 154(b) by 860 days.

(21) Appl. No.: 14/836,429

(22) Filed: Aug. 26, 2015

(65) Prior Publication Data

US 2016/0059048 A1 Mar. 3, 2016

Related U.S. Application Data

(60) Provisional application No. 62/042,698, filed on Aug. 27, 2014.

(51) Int. Cl.
*A62B 7/02* (2006.01)
*A62B 9/00* (2006.01)
(Continued)

(52) U.S. Cl.
CPC ................ *A62B 9/006* (2013.01); *A62B 7/02* (2013.01); *A62B 9/04* (2013.01); *G08B 21/0446* (2013.01); *G08B 25/016* (2013.01)

(58) Field of Classification Search
CPC .. A62B 7/02; A62B 9/006; A62B 9/04; G08B 21/0446; G08B 25/016
See application file for complete search history.

(56) References Cited

U.S. PATENT DOCUMENTS 5,045,839 A * 9/1991 Ellis .................. G08B 21/0415 340/309.7
5,157,378 A * 10/1992 Stumberg ............... A62B 9/006 2/8.1

(Continued)

FOREIGN PATENT DOCUMENTS

| | | | |
|---|---|---|---|
| EP | 2991052 | A1 | 3/2016 |
| EP | 2991052 | B1 | 8/2017 |
| WO | 2014052986 | A2 | 4/2014 |

OTHER PUBLICATIONS

European Search Report, EP Application No. 15182704.5, dated Dec. 10, 2015, 10 pages.

(Continued)

*Primary Examiner* — Joshua Lee
(74) *Attorney, Agent, or Firm* — Wick Phillips Gould & Martin, LLP

(57) ABSTRACT

Embodiments relate generally to personal alert safety systems (PASS) as well as motion detection systems and methods for motion detection. Some embodiments may comprise methods for determining the alarm status for a PASS, wherein a plurality of motion sensing elements may be utilized by a motion detection system, thereby reducing false alarms. A motion detection system may comprise two motion sensing elements, with one motion sensing element located near the chest and shoulders of a user, and one motion sensing element located near the hips and back of a user.

20 Claims, 8 Drawing Sheets

(51) Int. Cl.
*A62B 9/04* (2006.01)
*G08B 21/04* (2006.01)
*G08B 25/01* (2006.01)

(56) References Cited

U.S. PATENT DOCUMENTS

| | | | | |
|---|---|---|---|---|
| 5,492,110 | A * | 2/1996 | Lenz | A62B 9/006 116/67 R |
| 5,640,148 | A * | 6/1997 | Lewis | G08B 21/0453 200/61.74 |
| 5,697,099 | A * | 12/1997 | Siska, Jr. | A42B 3/046 2/422 |
| 5,757,273 | A * | 5/1998 | Crandall | A62B 9/006 340/573.1 |
| 5,781,118 | A * | 7/1998 | Wise | A62B 9/006 340/573.1 |
| 6,016,099 | A * | 1/2000 | Campman | G08B 21/0415 340/321 |
| 6,091,331 | A * | 7/2000 | Toft | A62B 9/00 340/321 |
| 6,198,394 | B1 | 3/2001 | Jacobsen et al. | |
| 6,703,939 | B2 * | 3/2004 | Lehrman | A61B 5/0205 340/669 |
| 7,005,980 | B1 | 2/2006 | Schmidt et al. | |
| 7,263,379 | B1 * | 8/2007 | Parkulo | G08B 21/02 340/501 |
| 8,006,877 | B2 * | 8/2011 | Lowry | A45F 3/04 224/262 |
| 8,573,982 | B1 | 11/2013 | Chuang | |
| 9,679,466 | B2 * | 6/2017 | Hogg | G08B 3/10 |
| 2002/0008625 | A1 * | 1/2002 | Adams | G08B 21/0211 340/573.1 |
| 2006/0049950 | A1 * | 3/2006 | Lockhart | A61B 5/1117 340/573.1 |
| 2006/0139166 | A1 * | 6/2006 | Choutier | A61B 5/0002 340/539.12 |
| 2012/0041279 | A1 | 2/2012 | Freeman et al. | |
| 2012/0194334 | A1 * | 8/2012 | Worthington | G08B 21/043 340/521 |
| 2013/0113620 | A1 * | 5/2013 | Hogg | A62B 9/006 340/539.12 |
| 2013/0257612 | A1 * | 10/2013 | Finet | A62B 9/006 340/539.11 |
| 2014/0163393 | A1 * | 6/2014 | McCombie | G16H 50/50 600/483 |
| 2015/0123785 | A1 * | 5/2015 | Haflinger | A61B 5/6831 340/539.11 |
| 2015/0273248 | A1 * | 10/2015 | Kuutti | A62B 9/00 128/201.12 |
| 2016/0173610 | A1 * | 6/2016 | Parkulo | G08B 25/016 340/573.1 |

OTHER PUBLICATIONS

EP Application No. 15182704.5, Communication pursuant to Rules 70(2) and 70a(2) and reference to Rule 39(1) EPC dated Mar. 7, 2016, 2 pages.

EP Application No. 15182704.5, Communication pursuant to Article 94(3) EPC dated May 2, 2016, 6 pages.

EP Application No. 15182704.5, Intention to Grant dated Apr. 10, 2017, 64 pages.

EP Application No. 15182704.5, Decision to Grant dated Jul. 27, 2017, 2 pages.

* cited by examiner

MULTI-SENSOR BASED MOTION SENSING IN SCBA

CROSS-REFERENCE TO RELATED APPLICATIONS

This application claims priority to U.S. Provisional Patent Application Ser. No. 62/042,698 (entitled MULTI-SENSOR BASED MOTION SENSING IN SCBA filed Aug. 27, 2014), which is incorporated herein by reference.

STATEMENT REGARDING FEDERALLY SPONSORED RESEARCH OR DEVELOPMENT

Not applicable.

REFERENCE TO A MICROFICHE APPENDIX

Not applicable.

BACKGROUND

A Personal Alert Safety System (PASS) device is commonly used by firefighters when entering a hazardous environment, such as a burning building. The PASS device is a small battery powered device that is carried with the user and will provide a loud audible alert and visual alert to notify others if the user is in distress. The PASS device can, for example, be attached to a backpack style harness for a Self-Contained Breathing Apparatus (SCBA), a turnout coat or other protective clothing worn by a firefighter. Typically, a PASS device can be activated manually or automatically (for example, manually by the user pressing a button, or automatically by a motion sensing device that activates the PASS device when the user has not moved in a certain amount of time), and the device will typically not turn itself off unless movement resets the PASS to the sensing mode and/or it is manually reset by pressing a reset button. According to National Fire Protection Association (NFPA) 1982:2013 standards, an activated PASS device must emit a high-pitched audible alert of at least 95 decibels at a distance of 3 meters from the device. The sound of an activated PASS device indicates a true emergency and should result in an immediate response to rescue the firefighter in distress.

SUMMARY

Aspects of the disclosure may include embodiments of a SCBA for use by emergency responders, comprising a backpack; a bottle of gas secured to the backpack; a motion detection system comprising a first motion sensing element, and a second motion sensing element; and at least one PASS, wherein the motion detection system receives motion information from the first motion sensing element and the second motion sensing element, wherein the motion detection system employs one or more methods to determine the motion status of a user and therefore the alarm status of the at least one PASS, and wherein the one or more methods utilize motion information from both the first motion sensing element and the second motion sensing element to determine alarm status.

In some embodiments, the first motion sensing element is located within a first PASS. In some embodiments, the second motion sensing element is located within a second PASS. In some embodiments, the SCBA may further comprise a heads-up display device, wherein the second motion sensing element is located within the heads-up display device. In some embodiments, the first motion sensing element is located on a first portion of the user's body, and wherein the second motion sensing element is located on a second portion of the user's body, different from the first portion of the user's body. In some embodiments, the first motion sensing element is located near the shoulders or chest of the user, and wherein the second motion sensing element is located near the hips of the user. In some embodiments, the motion detection system is operable to calculate a first vector sum of data received from the first motion sensing element; calculate a second vector sum of the data received from the second motion sensing element; and compare the two vector sums to a threshold value, wherein if the vector sum exceeds the threshold, motion is indicated. In some embodiments, the motion detection system is operable to check the motion detection of both the first motion sensing element and the second motion sensing element when determining alarm status.

Additional aspects of the disclosure may include embodiments of a motion detection system for use in combination with a SCBA, comprising a first motion sensing element; a second motion sensing element; and a computer system operable to receive information from the first motion sensing element and the second motion sensing element; communicate with a PASS of the SCBA; and determine alarm status for the PASS based on the received information from the motion sensing elements.

In some embodiments, the first motion sensing element is located near the shoulders and chest of a user. In some embodiments, the second motion sensing element is located near the hips of a user. In some embodiments, the computer system is further operable to determine the motion status for the first motion sensing element; determine the motion status for the second motion sensing element when the motion status for the first sensor indicates no-motion for a set time period; and communicate an alarm status to the PASS when the motion status of the second motion sensing element indicates no-motion for a set time period. In some embodiments, the first motion sensing element is located within a first PASS. In some embodiments, the second motion sensing element is located within a second PASS.

Other aspects of the disclosure may include embodiments of a method for determining the alarm status for a PASS, the method comprising receiving motion information from a motion detection system, the motion detection system comprising at least two motion sensing elements, during a preset time period; determining the motion status for a first motion sensing element; determining the motion status for a second motion sensing element; activating a PASS alarm when the motion status of both the first motion sensing element and the second motion sensing element indicate no-motion for a set time period; and continuing to receiving motion information from the motion detection system for a subsequent time period.

In some embodiments, the method may further comprise deactivating the PASS alarm when the motion status of the first motion sensing element indicates motion for the subsequent time period. In some embodiments, the method may further comprise deactivating the PASS alarm when the motion status of the second motion sensing element indicates motion for the subsequent time period. In some embodiments, the motion information is received in sample time periods. In some embodiments, a first motion sensing element is located near the shoulders and chest of a user. In some embodiments, a second motion sensing element is located near the hips of a user.

Other aspects of the disclosure may include embodiments of a SCBA for use by emergency responders, comprising: a backpack; a cylinder of air secured to the backpack; a motion detection system comprising: a first motion sensing element, and a second motion sensing element; and at least one PASS; wherein: the motion detection system receives motion information from at least one of the first motion sensing element and the second motion sensing element, the motion detection system employs one or more methods to determine the motion status of a user and therefore the alarm status of the at least one PASS, the one or more methods utilize motion information from both the first motion sensing element and/or the second motion sensing element to determine alarm status.

In some embodiments, the first motion sensing element may be located within a first PASS. In some embodiments, the second motion sensing element may be located within a second PASS. In some embodiments, the first PASS may be located on a first portion of the user's body. In some embodiments, the second PASS may be located on a second portion of the user's body, different from the first portion of the user's body. In some embodiments, the SCBA may further comprise a heads-up display device, wherein the second motion sensing element may be located within the heads-up display device. In some embodiments, the method may comprise calculating a vector sum of data received from both the first motion sensing element and the second motion sensing element. In some embodiments, the method may comprise checking the motion detection of both the first motion sensing element and the second motion sensing element when determining alarm status.

Other aspects of the disclosure may include embodiments of a motion detection system for use in combination with a SCBA, comprising: a first motion sensing element; a second motion sensing element; and a computer system operable to: receive information from the first motion sensing element and the second motion sensing element, communicate with a PASS, and determine alarm status for the PASS based on the received information from the motion sensing elements.

In some embodiments, the first motion sensing element may be located near the chest or the shoulders of a user. In some embodiments, the second motion sensing element may be located near the lower back or hips of a user. In some embodiments, the computer system may be further operable to: determine the motion status for the first motion sensing element; determine the motion status for the second motion sensing element when the motion status for the first sensor indicates no-motion for a set time period; and communicate an alarm status to the PASS when the motion status of the second motion sensing element indicates no-motion for a set time period. In some embodiments, the first motion sensing element may be located within a first PASS. In some embodiments, the second motion sensing element may be located within a second PASS.

Other aspects of the disclosure may include embodiments of a method for determining the alarm status for a PASS, the method comprising: receiving motion information from a motion detection system, the motion detection system comprising at least two motion sensing elements, wherein the motion information may be collected in motion sensing data samples over regular time periods; determining the motion status for a first motion sensing element; determining the motion status for a second motion sensing element when the motion status for the first sensor indicates no-motion for a set time period; and communicating an alarm status to the PASS when the motion status of the second motion sensing element indicates no-motion for a set time period.

In some embodiments, the method may further comprise resting the alarm status to the PASS when the motion status of the first motion sensing element indicates motion for a subsequent time period. In some embodiments, the method may further comprise resetting the alarm status to the PASS when the motion status of the second motion sensing element indicates motion for a subsequent time period. In some embodiments, the motion information is received in sample time periods. In some embodiments, a first motion sensing element is located within a first PASS. In some embodiments, a second motion sensing element is located within a second PASS.

These and other features will be more clearly understood from the following detailed description taken in conjunction with the accompanying drawings and claims.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

Figure 1A:
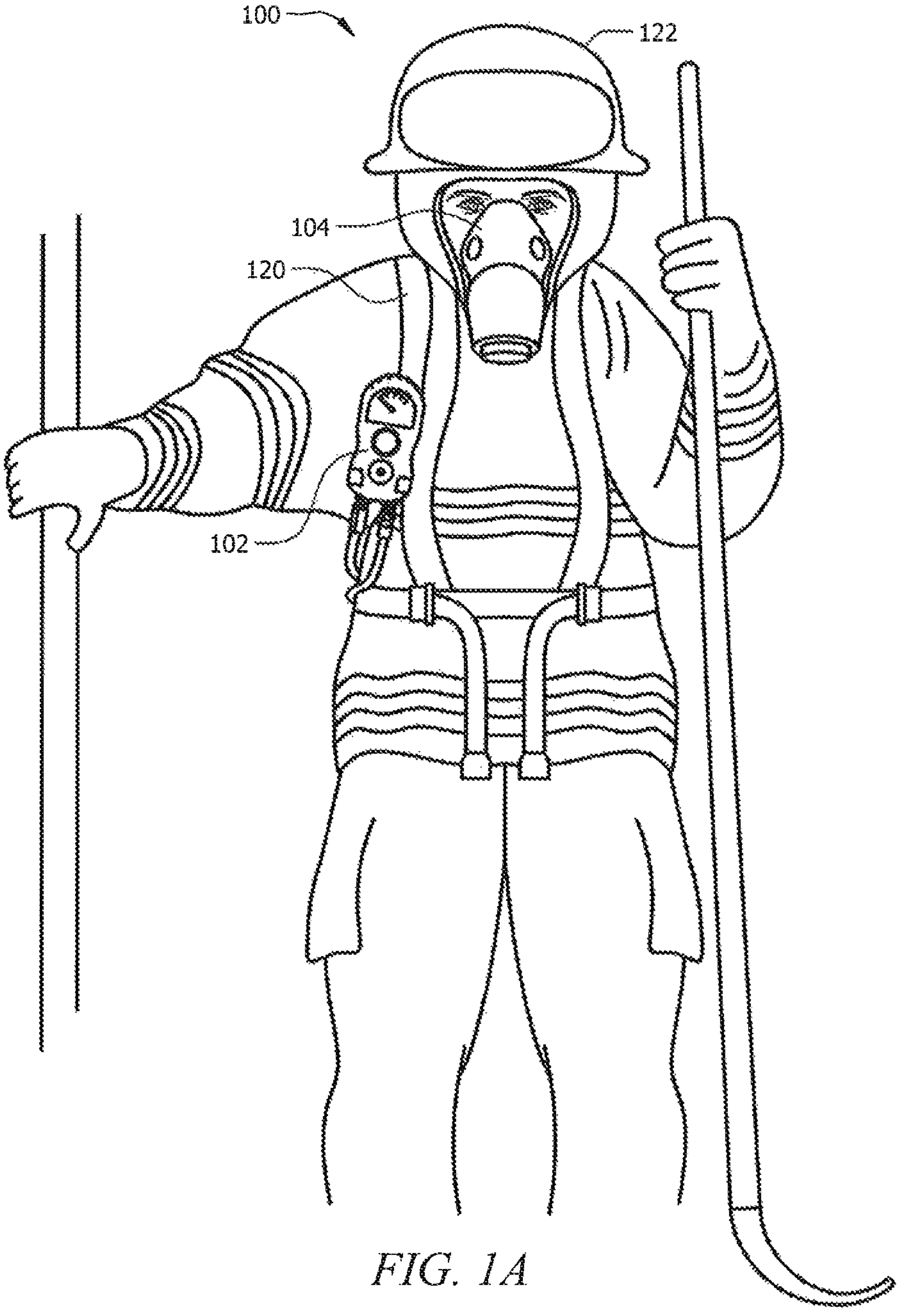
FIGS. 1A-1C illustrate an exemplary embodiment of a front PASS device and a heads-up display (HUD) integrated into an SCBA unit.

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The following brief definition of terms shall apply throughout the application:

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example;

The terms "about" or approximately" or the like, when used with a number, may mean that specific number, or alternatively, a range in proximity to the specific number, as understood by persons of skill in the art field; and If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

Embodiments relate generally to PASS and motion detection associated with a PASS device. A PASS device may be located anywhere on a user, and may typically be attached to personal protective equipment, such as protective clothing or an SCBA, that the user may already be wearing based on the type of hazardous environment to be entered by the user. Typically, motion detection in a PASS device may be accomplished by one or more motion sensing element (such as a mercury switch, ball sensor, 2-axis accelerometer, or 3-axis accelerometer, for example). Accurate motion sensing may depend on the placement of the sensing element and the mounting method of the PASS device. For example, the PASS device may be located near the hip (or lower back) region or chest (or shoulder) region of a user. Motion detected from the user while working (and wearing the PASS device) may vary depending on the use case scenario and the location of the PASS device. In some cases, it may be difficult to determine a threshold level of motion for alert, resulting in false alerts that the user must then manually cancel using their hands to either shake the PASS or press the reset button and/or considerable movement of the body. This may be a hindrance to a user, especially in a rescue scenario, as the alert would emit at a high decibel level. False alerts may also drain the battery life of the PASS device and may make workers around the false alarm become immune to the alert, thereby causing users to ignore the alert.

In some embodiments, measures may be taken to prevent false alerts from a PASS device based on the motion sensing element(s). For example, at least two motion sensing elements may be used in a motion sensing system, wherein one or more motion detection methods may be employed to determine alerts based on the input from both of the at least two motion sensing elements. Both motion sensing elements may be used to deactivate an alarm, and motion from both elements may be constantly monitored. In some testing of systems using two motion sensing elements, false alarms were reduced by about 70%. In other words, the time that the PASS device is in sensing mode, and not alarm mode, was increased by 70%.

The motion sensing elements may be located on different parts of the body, with one located on the upper body of a user, and one located on the lower body of the user. In some embodiments, one motion sensing element may be located on the shoulders and/or chest of a user, while the other motion sensing element is located on the lower back and/or hips of a user. The motion sensing element located on the chest of the user may also be easier accessed by a user's hands. By having the two motion sensing elements located on separate parts of the body, the accuracy of the motion sensing is improved. While working, usually at least one of the locations will be in motion. And if both locations are stationary for a period of time, triggering a false alarm, a user should be able to move one of the locations to deactivate the false alarm.

For example, if a user is using their arms/hands to work on something and therefore cannot move the motion sensing element near the chest/shoulders, their lower body should be free to move to deactivate the alarm. Similarly, if a user is crawling or crouching, and one location is inaccessible or unmovable, the other location should be able to be moved and/or accessed by the user.

Figure 1B:
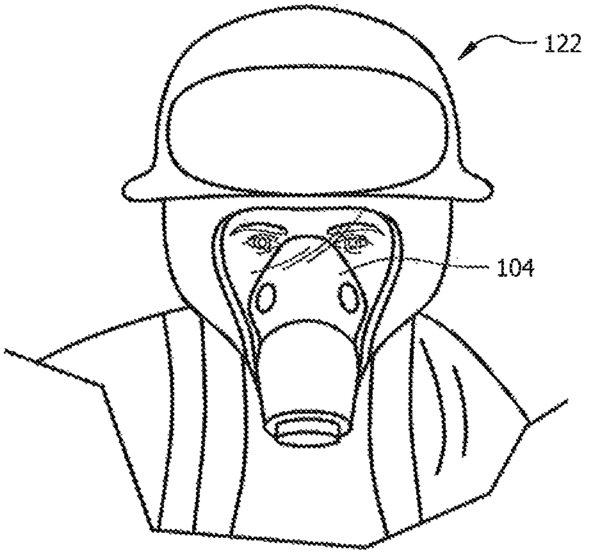
Figure 1C:
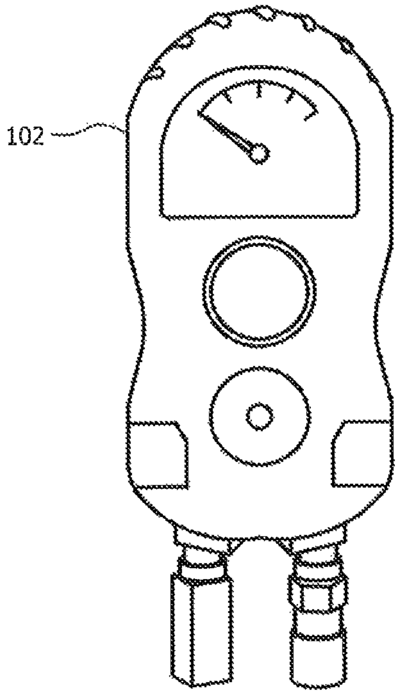

FIGS. 1A-1C illustrate an exemplary embodiment of a SCBA unit 100 comprising a front PASS device 102, possibly attached to the backpack 120 of the SCBA 100, and a heads-up display (HUD) device 104 attached to the mask portion 122 of the SCBA 100. The front PASS device 102 may be located in a position on the backpack 120 to allow for access by the user, which may be necessary if the PASS device could be manually activated, for example. The PASS device could be armed manually or automatically, and in some embodiments, the PASS device 102 may be integrated into an SCBA 100 such that the PASS device 102 may be initially armed when a user opens the air circuit of a SCBA unit 100. In some embodiments, the PASS device 102 may be attached to other portions of the SCBA such as a belt section of the SCBA backpack 120. Either location may allow for easy access by a user. In some embodiments, the SCBA unit 100 may further comprise other components, such as a mask 122, a head harness, air circuits, adjustment buckles for the backpack 120, and other such components as would be understood by a person of skill in the art to be included in an SCBA unit.

Figure 2A:
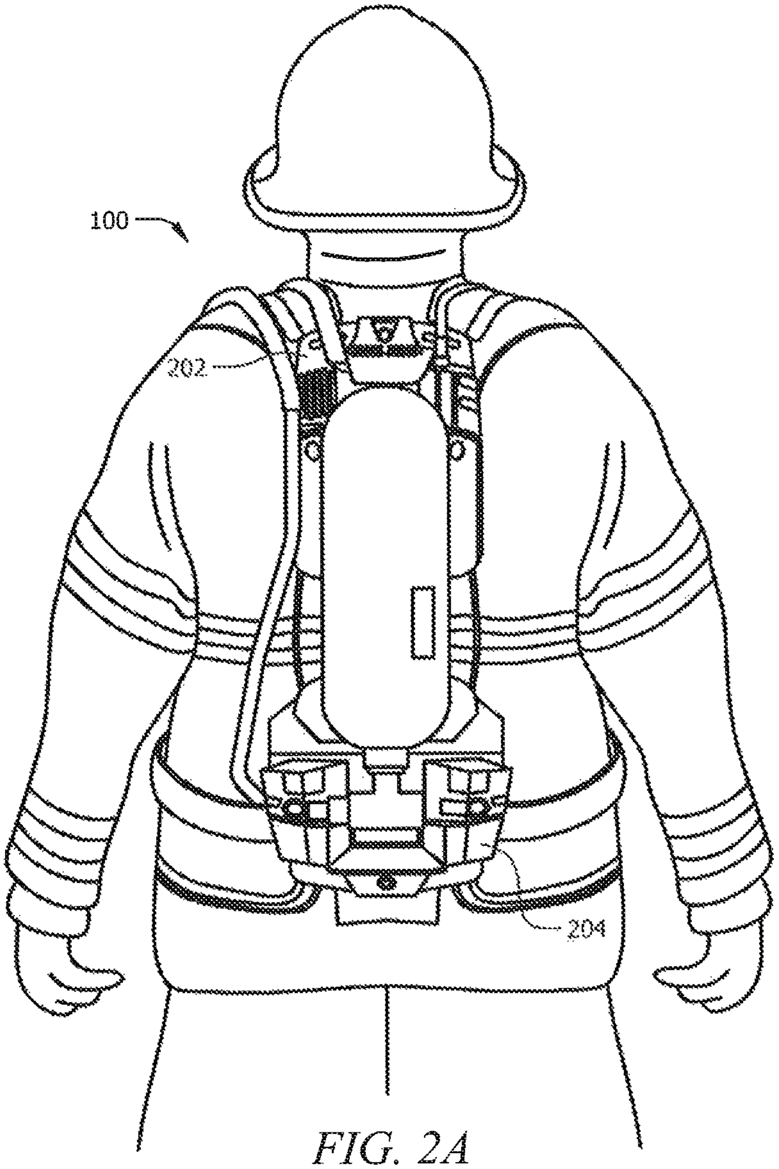
FIGS. 2A-2C illustrate exemplary embodiments of a back PASS device integrated into an SCBA unit.
Figure 2B:
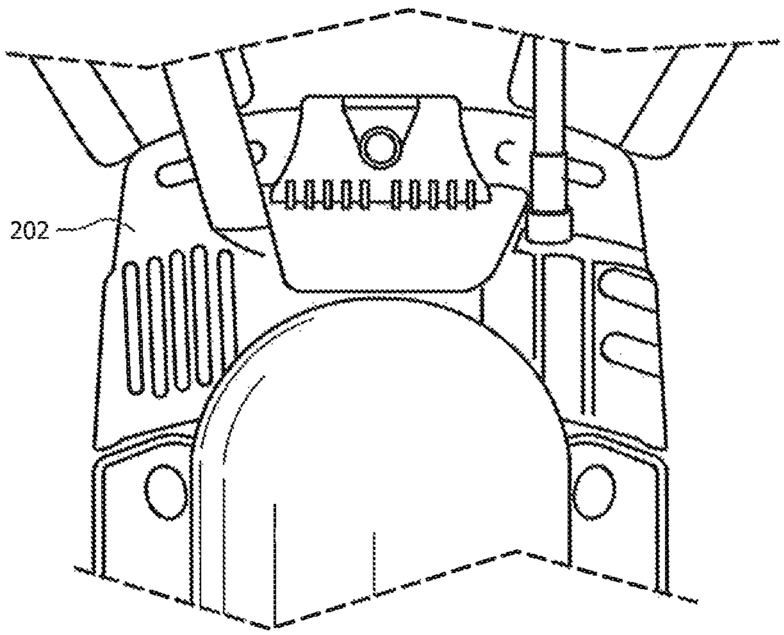
Figure 2C:
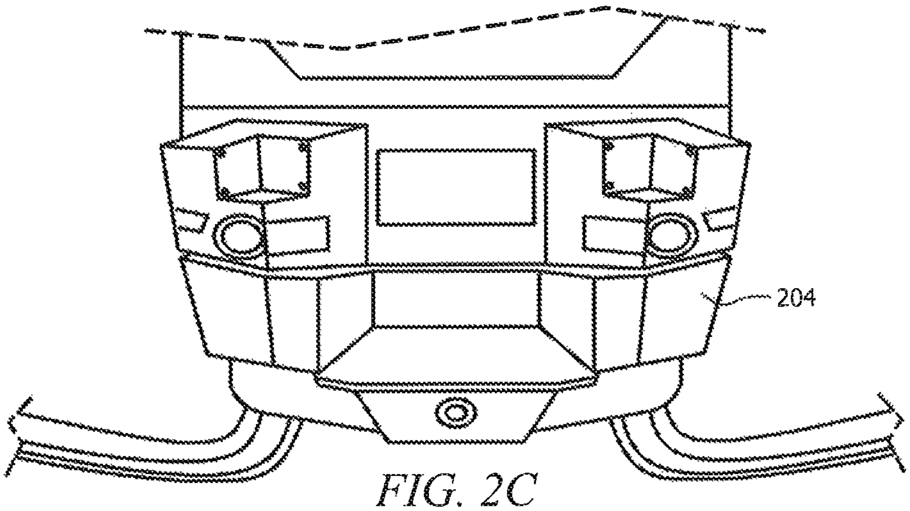

FIGS. 2A-2C illustrate another view of the SCBA 100, wherein the SCBA 100 may comprise a back PASS 202 and 204. In some embodiments, the back PASS 202 may be located at the top (or upper portion) of the backpack 120 portion of the SCBA 100 near a user's shoulders or chest. In other embodiments, the back PASS 204 may be located at the bottom (or lower portion) of the backpack 120 portion of the SCBA 100, near a user's hips or lower back.

Figure 3:
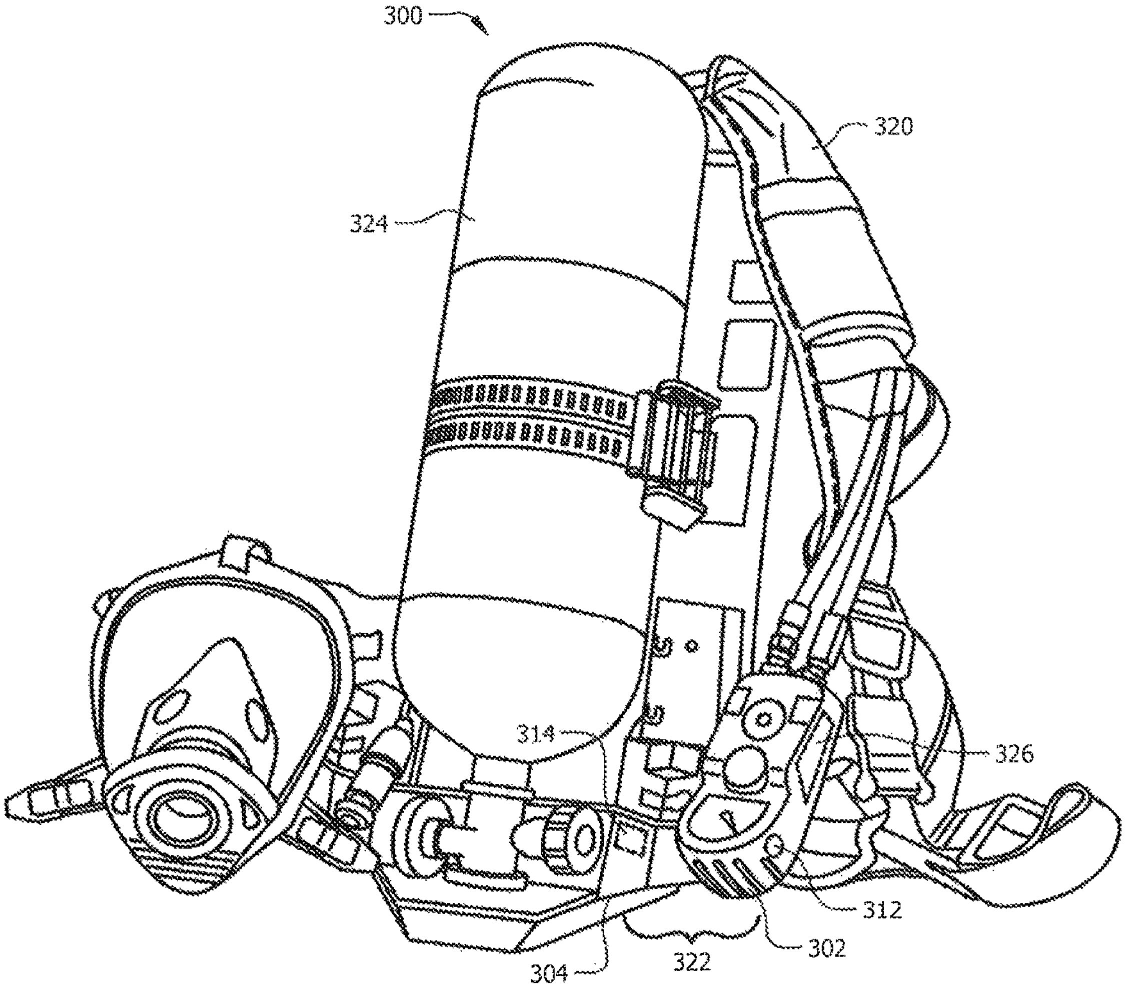
FIG. 3 illustrates an embodiment of an SCBA unit comprising a motion detection system.

In the embodiment shown in FIG. 3, the SCBA 300 may comprise a front PASS 302 (which may be similar to the front PASS 102) and a back PASS 304 (which may be similar to the back PASS 202 or 204, and may be located at the lower or upper portion of the backpack) attached to the backpack 320 portion of the SCBA 300. In the embodiment of FIG. 3, the front PASS 302 may comprise a first motion sensing element 312 and back PASS 304 may comprise a second motion sensing element 314. In some embodiments, a motion detection system 322 may utilize the inputs from both of the motion sensing elements 312 and 314. In the embodiment of FIG. 3, the motion detection system 322 may be a part of the front PASS 302. However, in other embodiments, the motion detection system 322 may be located on another part of the SCBA 300, such as the back PASS 304, as well as separate from the SCBA 300, such as a remote computer system that receives information from the motion sensing elements of the front PASS 302 and the back PASS 304. In some embodiments, one or more of the PASS devices 302 and 304 may comprise a computer system 326 for receiving and processing information from the motion sensing elements 312 and 314. In some embodiments, the at least two motion sensing elements may be located in other portions of the SCBA 300, such as an HUD device (described above), the helmet and/or of the SCBA, among other locations. In the embodiment shown in FIG. 3, the motion sensing elements may be located near the shoulders and hips of a user, because areas of the body may be more easily moved by a user to reset a false alarm.

The at least two motion sensing elements may be used in combination to determine alerts issued by one or both of the front PASS 302 and back PASS 304. In some embodiments, the motion detection from both of the motion sensing elements may be considered when determining an alert, as illustrated in the table below:

| Front PASS 302 | Back PASS 304 | System Movement Detection |
|---|---|---|
| Motion detected | Motion detected | Motion Detected |
| Motion detected | No-motion detected | Motion Detected |
| No-motion detected | Motion detected | Motion Detected |
| No-motion detected | No-motion detected | No-Motion Detected |

In other words, if motion is detected by both the front PASS 302 and the back PASS 304, the system 322 may register detected motion. If motion is detected by the front PASS 302 and not detected by the back PASS 304, the system 322 may register detected motion. Similarly, if motion is not detected by the front PASS 302 but is detected by the back PASS 304, the system 322 may register detected motion. If no motion is detected by either the front PASS 302 or the back PASS 304, the system may register no detected motion, wherein an alert may then be issued by the system to one or both of the front PASS 302 and back PASS 304.

Figure 4:
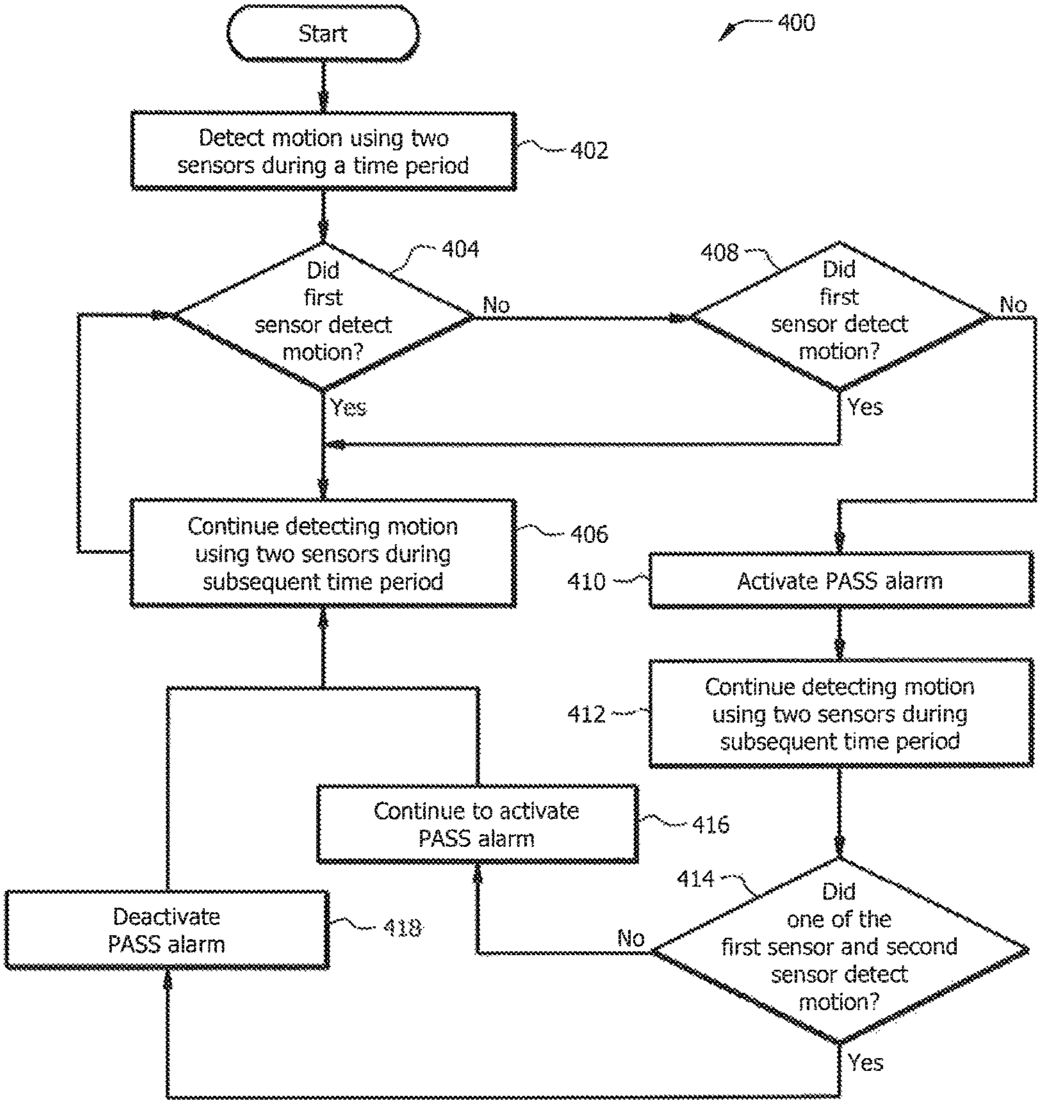
FIG. 4 illustrates an exemplary embodiment of method for detecting motion from one or more motion sensing elements.

FIG. 4 illustrates a method 400 for determining alert station in a motion detection system (such as motion detection system 322) that comprises at least two motion sensing elements. At step 402, the motion detection system may detect motion using two sensors during a preset time period. This time period may be about 10 seconds, about 20 seconds, about 30 seconds, or any other appropriate time period. The sensing time period may be adjusted based on the user's needs.

At step 404, it may be determined if a first sensor (of the two sensors) detects motion. If the first sensor detects motion, at step 406, the motion detection system may continue to detect motion using the two sensors for subsequent time periods, and the method 400 may return step 404. If the first sensor does not detect motion, at step 408, it may be determined if a second sensor (of the two sensors) detects motion. Both motion sensing elements may be sending information If the second sensor detects motion, at step 406, the motion detection system may continue to detect motion using the two sensors for subsequent time periods and the method 400 may return step 404. If the second sensor does not detect motion, at step 410, a PASS alarm may be activated, wherein the alarm indicates lack of motion from the user.

After the alarm is activated, at step 412, the motion detection system may continue detecting motion using the two sensors for subsequent time periods. In some embodiments, the time period may be shorter if the PASS alarm is activated. At step 414, it may be determined if at least one of the first and second motion detectors detects motion. If one of the motion sensing elements detects motion, at step 418, the alarm may be deactivated. This may allow a user to intentionally move one or both of the motion sensing elements after the alarm has been activated, if the user is not in danger or in need of help, thereby deactivating the unnecessary alarm. Then, at step 406, the motion detection system may continue to detect motion using the two sensors for subsequent time periods and the method 400 may return step 404.

If one of the motion sensing elements does not detect motion, at step 416, the PASS alarm may continue to be activated. Then, at step 406, the motion detection system may continue to detect motion using the two sensors for subsequent time periods and the method 400 may return step 404.

Figure 5:
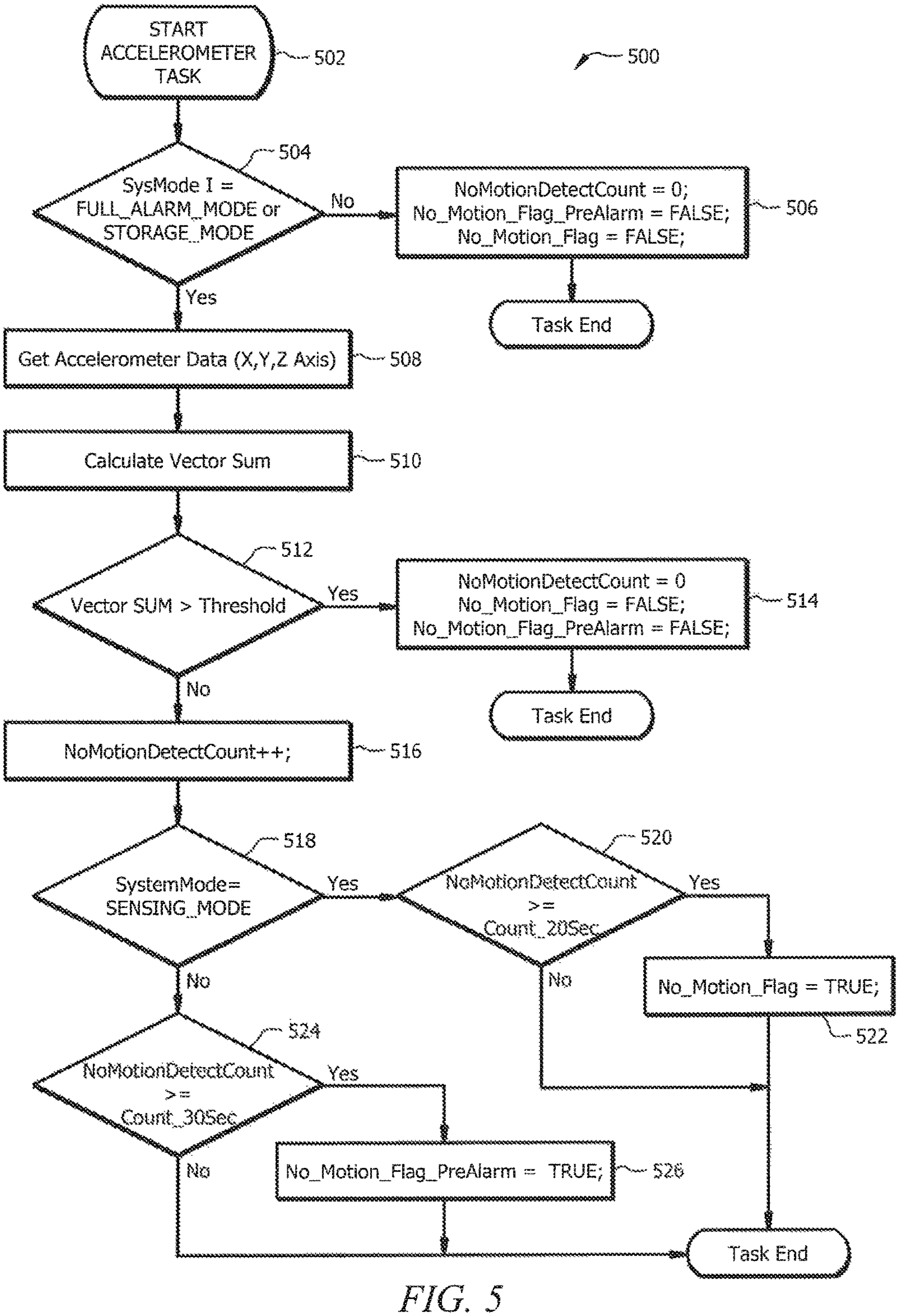
FIG. 5 illustrates another exemplary embodiment of method for detecting motion from one or more motion sensing elements.

FIG. 5 illustrates a method 500 for determining alert status in a motion detection system (such as motion detection system 322) that comprises at least two motion sensing elements. The method may use samples collected at a rate of 40 milliseconds (or 25 samples per second). Additionally, the method may assume that the maximum human motion frequency is 5 Hz.

At step 502, the method may start. At step 504, the method may determine if the system mode is not in FULL_ALARM_MODE or STORAGE_MODE, wherein a YES result may indicate that the system is in neither full alarm mode nor storage mode, and a NO result may indicate that the system is in one of either of those modes and the motion detection system is turned off. If step 504 produces a NO result, at step 506, the no-motion detection count may be zero, the no-motion flag pre-alarm may be FALSE, and the no-motion flag may be FALSE. Then the task may end. If step 504 produces a YES result, at step 508, a request for accelerometer data (from the motion sensing elements) may be initiated. Then, at step 510, a vector sum may be calculated from the requested data (wherein the vector sum may combine the motion sensing data from the plurality of motion sensing elements). At step 512, it may be determined whether the calculated vector sum is greater than a predetermined threshold. If step 512 produces a YES (i.e. the vector sum is greater than the threshold), at step 514 the no-motion detection count may be zero, the no-motion flag pre-alarm may be FALSE, and the no-motion flag may be FALSE. Then the task may end. If step 512 produces a NO (i.e. the vector sum is not greater than the threshold), at step 516, the no-motion detection count may be determined.

At step 518, it may be determined if the system mode is in SENSING_MODE. If step 518 produces a YES, at step 520, it may be determined if the no-motion detection count (determined at step 516) is greater than or equal to the sample count for a sample time of about 20 seconds (Count_20Sec). In some embodiments, the sample time may be more than 20 seconds or less than 20 seconds, wherein the sample time may be dependent on the power and the age of the batteries being used in the PASS. In some embodiments, the sample count for about 20 seconds may be equivalent to about 500, wherein a sample is taken every 40 milliseconds. In some embodiments, a YES from step 520 may indicate that a user has not moved within the last 20 seconds. If step 520 produces a YES, the no-motion flag may be TRUE at step 522 and the task may end. In some embodiments, a TRUE no-motion flag at step 522 may trigger an alarm to one of the PASS devices. In some embodiments, a NO from step 520 may indicate that a user has moved within the last 20 seconds. If step 520 produces a NO, the task may end.

If step 518 produces a NO, at step 524, it may be determined if the no-motion detection count (determined at step 516) is greater than or equal to the sample count for a sample time of about 30 seconds (Count_30Sec). In some embodiments, the sample time may be more than 30 seconds or less than 30 seconds, wherein the sample time may be dependent on the power and the age of the batteries being used in the PASS. In some embodiments, the sample count for about 30 seconds may be equivalent to about 750, wherein a sample is taken every 40 milliseconds. In some embodiments, a YES from step 524 may indicate that a user has not moved within the last 30 seconds. If step 524 produces a YES, the no-motion flag may for a pre-alarm be TRUE at step 526 and the task may end. In some embodiments, a TRUE no-motion flag for pre-alarm at step 526 may trigger a pre-alarm to one of the PASS devices. In some embodiments, a NO from step 524 may indicate that a user has moved within the last 30 seconds. If step 524 produces a NO, the task may end.

Figure 6:
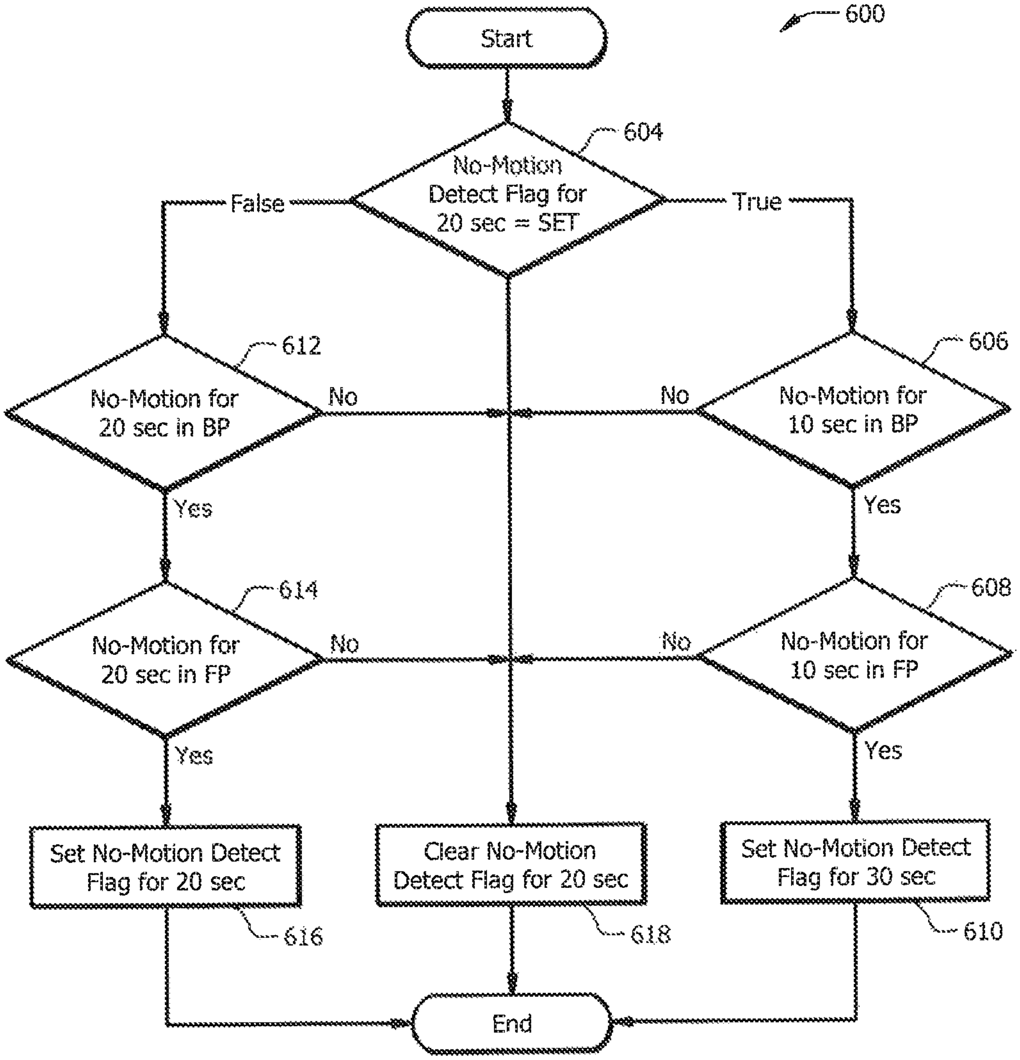
FIG. 6 illustrates yet another exemplary embodiment of method for detecting motion from one or more motion sensing elements.

FIG. 6 illustrates a method 600 for determining "man-down" status in a motion detection system (such as motion detection system 322) that comprises at least two motion sensing elements. At step 604, it may be determined if a no-motion detection flag for a sample time of about 20 seconds has been triggered. In some embodiments, the sample time may be more than 20 seconds or less than 20 seconds, wherein the sample time may be dependent on the power and the age of the batteries being used in the PASS. If the result of step 604 is TRUE (meaning that the no-motion detection flag for 20 seconds has been triggered), at step 606, it may be determined if there has been no motion for a sample time of about 10 seconds in the back PASS (BP) of the system. In some embodiments, the sample time may be more than 10 seconds or less than 10 seconds, wherein the sample time may be dependent on the power and the age of the batteries being used in the PASS. If the result of step 606 is NO (meaning there was detected motion in the back PASS in the 10 seconds), at step 618, the no-motion detection flag for 20 seconds may be cleared and the task may end. If the result of step 606 is YES (meaning that no motion was detected in the back PASS in the 10 seconds), at step 608, it may be determined if there has been no motion for a sample time of about 10 seconds in the font PASS (FP) of the system. In some embodiments, the sample time may be more than 10 seconds or less than 10 seconds, wherein the sample time may be dependent on the power and the age of the batteries being used in the PASS. If the result of step 608 is NO (meaning there was detected motion in the front PASS in the 10 seconds), at step 618, the no-motion detection flag for 20 seconds may be cleared and the task may end. If the result of step 608 is YES (meaning that no motion was detected in the front PASS in the 10 seconds), at step 610, the no-motion detection flag may be set for 30 seconds, and the task may end.

If the result of step 604 is FALSE (meaning that the no-motion detection flag for 20 seconds has not been triggered), at step 612, it may be determined if there has been no motion for a sample time of about 20 seconds in the back PASS (BP) of the system. In some embodiments, the sample time may be more than 20 seconds or less than 20 seconds, wherein the sample time may be dependent on the power and the age of the batteries being used in the PASS. If the result of step 612 is NO (meaning there was detected motion in the back PASS in the 20 seconds), at step 618, the no-motion detection flag for 20 seconds may be cleared and the task may end. If the result of step 612 is YES (meaning that no motion was detected in the back PASS in the 20 seconds), at step 614, it may be determined if there has been no motion for a sample time of about 20 seconds in the font PASS (FP) of the system. In some embodiments, the sample time may be more than 20 seconds or less than 20 seconds, wherein the sample time may be dependent on the power and the age of the batteries being used in the PASS. If the result of step 614 is NO (meaning there was detected motion in the front PASS in the 20 seconds), at step 618, the no-motion detection flag for 20 seconds may be cleared and the task may end. If the result of step 614 is YES (meaning that no motion was detected in the front PASS in the 20 seconds), at step 616, the no-motion detection flag may be set for 20 seconds, and the task may end.

Both of the methods of FIGS. 5 and 6 may be completed continuously or periodically while a user is wearing an SCBA and PASS device(s) as described above. The methods may be completed to determine the motion of a user, and based on detected no-motion, issue alerts to one of the PASS devices.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow, that scope including all equivalents of the subject matter of the claims. Each and every claim is incorporated as further disclosure into the specification and the claims are embodiment(s) of the present invention(s). Furthermore, any advantages and features described above may relate to specific embodiments, but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure. Specifically and by way of example, although the headings might refer to a "Field," the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as comprises, includes, and having should be understood to provide support for narrower terms such as consisting of, consisting essentially of, and comprised substantially of. Use of the term "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A Self-Contained Breathing Apparatus (SCBA) for use by emergency responders, comprising:
- a backpack;
- a bottle of gas secured to the backpack;
- a motion detection system comprising:
  - a first motion sensing element, and
  - a second motion sensing element; and
- at least one Personal Alert Safety System (PASS) comprising an alarm, wherein:
- the motion detection system receives motion information from the first motion sensing element and the second motion sensing element,
- the motion detection system employs one or more methods to determine the motion status of a user and therefore the alarm status of the at least one PASS,
- the one or more methods utilize motion information from both the first motion sensing element and the second motion sensing element to determine alarm status, and
- the motion detection system activates the alarm associated with the at least one PASS only when both the first motion sensing element and the second motion sensing element indicate no motion for a set time period.

2. The SCBA of claim 1, wherein the first motion sensing elements located within a first PASS.

3. The SCBA of claim 2, wherein the second motion sensing element is located within a second PASS.

4. The SCBA of claim 2, further comprising a heads-up display device, wherein the second motion sensing element is located within the heads-up display device.

5. The SCBA of claim 1, wherein the first motion sensing element is located on a first portion of the user's body, and wherein the second motion sensing element is located on a second portion of the user's body, different from the first portion of the user's body.

6. The SCBA of claim 1, wherein the first motion sensing element is located near the shoulders or chest of the user, and wherein the second motion sensing element is located near the hips of the user.

7. The SCBA of claim 1, wherein the motion detection system is operable to:
- calculate a first vector sum of data received from the first motion sensing element;
- calculate a second vector sum of the data received from the second motion sensing element; and
- compare the two vector sums to a threshold value, wherein if the vector sum exceeds the threshold, motion is indicated.

8. The SCBA of claim 1, wherein the first motion sensing element and the second motion sensing element are configured for location on different portions of a user's body.

9. The SCBA of claim 1, wherein, subsequent to activation of the alarm, the motion detection system continues to utilize motion information from both the first motion sensing element and the second motion sensing element to determine alarm status for a subsequent time period and deactivates the alarm when the at least one of the first motion sensing element and the second motion sensing element indicates motion.

10. A motion detection system for use in combination with a Self-Contained Breathing Apparatus (SCBA), comprising:
- a first motion sensing element;
- a second motion sensing element; and
- a computer system operable to:
  - receive information from the first motion sensing element and the second motion sensing element;
  - communicate with a Personal Alert Safety System (PASS) of the SCBA;
  - determine alarm status for the PASS based on the received information from the motion sensing element; and
  - activate an alarm only when both the first motion sensing element and the second motion sensing element indicate no motion for a set time period.

11. The motion detection system of claim 10, wherein the first motion sensing element is located near the shoulders and chest of a user.

12. The motion detection system of claim 10, wherein the second motion sensing element is located near the hips of a user.

13. The motion detection system of claim 10, wherein the computer system is further operable to:
- determine the motion status for the first motion sensing element;
- determine the motion status for the second motion sensing element when the motion status for the first sensor indicates no-motion for a set time period; and
- communicate an alarm status to the PASS when the motion status of the second motion sensing element indicates no- motion for a set time period.

14. The motion detection system of claim 10, wherein the first motion sensing element is located within a first PASS.

15. The motion detection system of claim 14, wherein the second motion sensing element is located within a second PASS.

16. The motion detection system of claim 10, wherein the first motion sensing element is configured for location on an upper portion of a user's body and the second motion sensing element is configured for location on a lower portion of the user's body.

17. The motion detection system of claim 10, wherein the computer system is further operable to, subsequent to activation of the alarm, continue to receive information from the first motion sensing element and the second motion sensing element and deactivate the alarm when the at least one of the first motion sensing element and the second motion sensing element indicates motion.

18. A method for determining the alarm status for a Personal Alert Safety System (PASS) associated with a Self-Contained Breathing Apparatus (SCBA), the SCBA comprising a motion detection system, the motion detection system comprising a first motion sensing element and a second motion sensing element, the method comprising:
- receiving motion information from the detection system during a preset time period;

determining the motion status for the first motion sensing element;

determining the motion status for the second motion sensing element;

activating a PASS alarm when the notion status of both the first motion sensing element and the second motion sensing element indicate no-motion for a set time period; and continuing to receiving motion information from the motion detection system for a subsequent tune period.

19. The method of claim 18, further comprising deactivating the PASS alarm when the motion status of the first motion sensing element indicates motion for the subsequent time period.

20. The method of claim 18, wherein the SCBA further comprises:

a backpack;

a bottle of gas secured to the backpack; and the PASS.

* * * * *